United States Patent [19]

Ribner et al.

[11] Patent Number: 5,430,784
[45] Date of Patent: Jul. 4, 1995

[54] COMPUTERIZED TOMOGRAPHY IMAGING USING MULTI-SLICE DETECTOR WITH SELECTABLE SLICE THICKNESS

[75] Inventors: David B. Ribner, Schenectady, N.Y.; Michael A. Wu, Oro Valley, Ariz.

[73] Assignee: General Electric Company, Schenectady, N.Y.

[21] Appl. No.: 203,076

[22] Filed: Feb. 28, 1994

[51] Int. Cl.[6] .................................. G21K 1/12
[52] U.S. Cl. ................................ 378/19; 378/4
[58] Field of Search ............ 378/4, 10, 11, 17, 19, 378/20

[56] References Cited

U.S. PATENT DOCUMENTS

| | | | |
|---|---|---|---|
| 4,112,303 | 9/1978 | Brandt | 250/445 |
| 4,115,695 | 9/1978 | Kelman | 250/445 |
| 4,583,240 | 4/1986 | Gatten et al. | 378/19 |
| 4,965,726 | 10/1990 | Heuscher et al. | 378/19 X |
| 4,991,189 | 2/1991 | Boomgaarden et al. | 378/4 |
| 5,012,498 | 4/1991 | Cuzin et al. | 378/19 X |
| 5,228,069 | 7/1993 | Arenson et al. | 378/19 |
| 5,241,576 | 8/1993 | Lonn | 378/19 |

*Primary Examiner*—David P. Porta
*Attorney, Agent, or Firm*—Enrique J. Mora; Marvin Snyder

[57] ABSTRACT

A computerized tomography system includes a detector array made up of a set of detector subelements aligned along a slice thickness direction. A controllable switching matrix selectively interconnects a predetermined number of successive detector subelements to a respective summing amplifier to produce slice-constituent signals which measure a respective slice positioned to pass through a body. Each respective slice having a selectable thickness in a region of interest to be imaged.

25 Claims, 7 Drawing Sheets

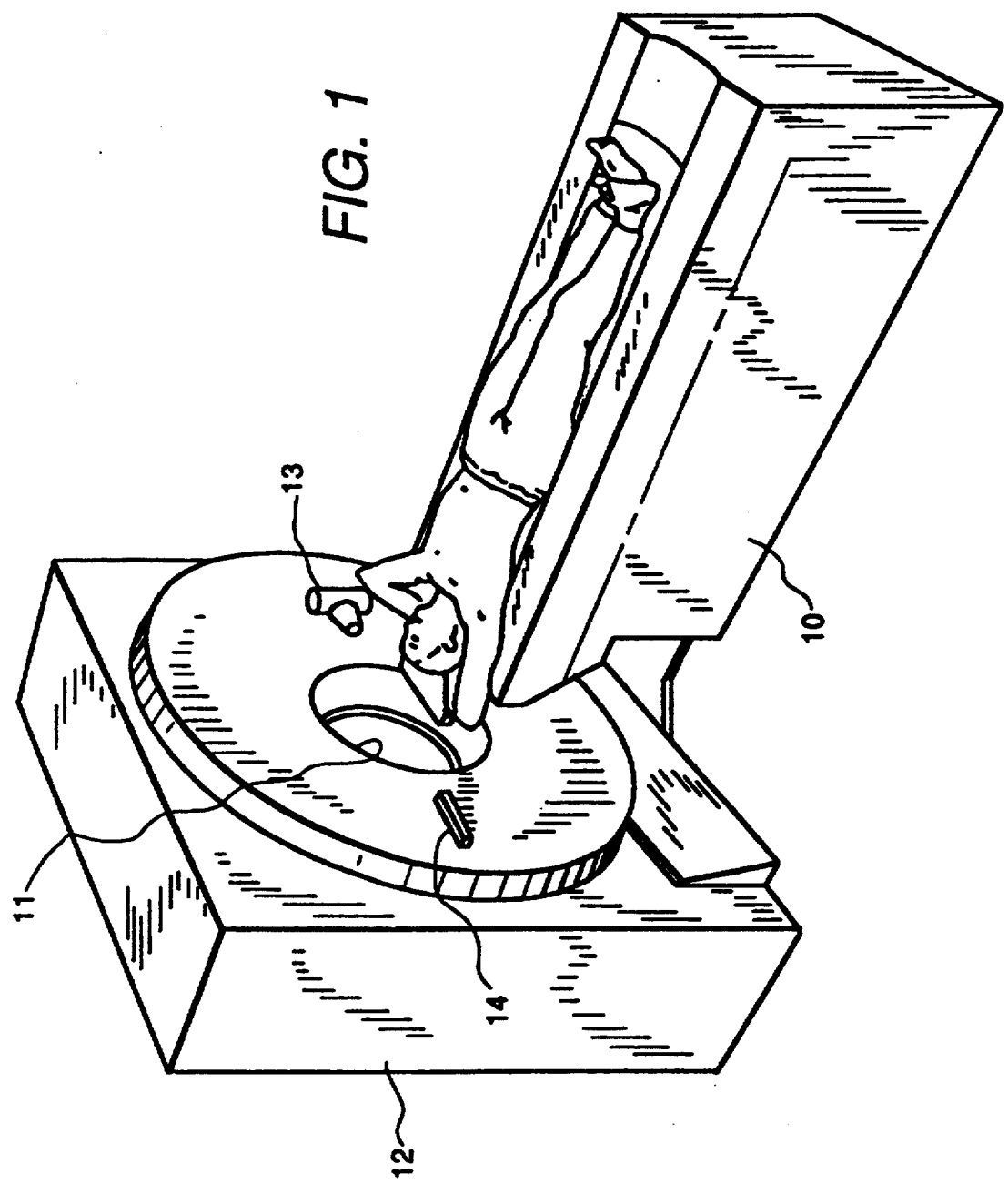

COMPUTERIZED TOMOGRAPHY IMAGING USING MULTI-SLICE DETECTOR WITH SELECTABLE SLICE THICKNESS

BACKGROUND OF THE INVENTION

The field of the present invention is generally related to computed tomography and, particularly, computerized tomography (CT) imaging using a multi-slice detector with selectable slice thickness.

In a conventional CT system used to produce images of at least a region of interest of the human anatomy a complete scan of the patient is comprised of a set of x-ray attenuation measurements which are made at discrete angular orientations of the x-ray source and detector. Each such set of measurements is referred to in the art as a "view" and the results of each such set of measurements is a transmission profile. The set of measurements in each view may be obtained by simultaneously translating the x-ray source and detector across the acquisition field of view. As the devices are translated, a series of x-ray attenuation measurements is made through the patient and the resulting set of data provides a transmission profile at one angular orientation. The angular orientation of each of the x-ray source and detector is then changed (for example, incremented by 1°) and another view is acquired. In an alternative structure for acquiring each transmission profile, the x-ray source produces a fan-shaped beam which defines a plane that passes through the patient and impinges on a generally arcuate array of detectors situated in the plane of the beam. In a conventional detector array, each detector in the array typically produces a separate attenuation signal and the signals from all the detectors are separately acquired to produce the transmission profile for the indicated angular orientation. As in the first structure, the x-ray source and array detector are then revolved to a different angular orientation and the next transmission profile is acquired.

The acquired transmission profiles are then used to reconstruct an image which indicates the x-ray attenuation coefficient of each voxel or volumetric element in the reconstruction field of view. These attenuation coefficients are convened to integers called "CT numbers," which are used to control the brightness of a corresponding pixel on a CRT display. An image which reveals the anatomical structures in a slice taken through the patient and oriented normal to the axis of the gantry aperture is thus produced.

In clinical applications the thickness of the slice taken through the patient may be varied from relatively thin (1 mm) to relatively thick (10 mm). The slice thickness is typically controlled by an adjustable collimation device which is positioned between the patient and the x-ray source. One such collimation device is described in U.S. Pat. No. 4,991,189 issued Feb. 5, 1991, which is owned by the assignee of the present invention.

As the thickness of the slice is increased, the reconstructed image becomes more susceptible to partial volume artifacts. The CT number at each image pixel represents the attenuation of a given x-ray beam portion passing by the corresponding voxel in the patient. For infinitesimally thin beams, an accurate measurement of the line integral attenuation along the x-ray beam could be made, provided sufficient imaging energy can be detected, so that the CT number reflects a true average attenuation introduced by all of the material in the corresponding patient voxel. However, for x-ray beams having a finite thickness, and where the attenuation introduced by the material is substantially inhomogeneous in the thickness direction, an accurate measurement of the average x-ray beam attenuation across the beam thickness direction is not achieved. This inaccuracy is especially pronounced, for example, in voxels which contain a boundary between highly attenuating material such as bone and soft tissues. Because of the nature of the image reconstruction process, this inaccuracy not only affects the corresponding image pixel, but also surrounding pixels. This results in image artifacts which interfere with the diagnosis of soft tissue features.

U.S. Pat. No. 5,241,576, issued Aug. 31, 1993 owned by the assignee of the present invention and which is herein incorporated by reference, describes an x-ray CT scanner which, in conjunction with logarithmic preprocessing techniques, can produce images from one or more slices of attenuation data with reduced partial volume artifacts. It is desirable to provide an improved CT system which eliminates the need for such logarithmic pre-processing techniques and yet is capable of conveniently utilizing a multi-slice detector. It is further desirable to provide a switching technique which allows for selecting slice thickness with a reduced number of electronic circuits and which in turn improves the overall signal-to-noise ratio of the system with the benefit of lower x-ray dose to the patient.

SUMMARY OF THE INVENTION

Generally speaking, the present invention fulfills the foregoing needs by providing an imaging system, such as a computerized tomography system or other similar imaging system, for imaging at least a region of interest in a body, such as a patient or inanimate object. The system comprises a source of imaging energy for producing a beam of imaging energy along a beam axis and having a predetermined thickness in a direction orthogonal to the beam axis. An array detector is positioned to receive the beam of imaging energy and includes a set of detector subelements aligned with each other along the beam thickness direction to receive successive portions of the beam of energy along its thickness direction to produce a corresponding set of thin-slice attenuation signals. A switching matrix is coupled to the set of detector subelements to receive each thin-slice attenuation signal and to selectively interconnect a predetermined number of detector subelements to produce at least one set of interconnect thin-slice attenuation signals. As used herein the expression "interconnect thin-slice attenuation signals" refers to thin-slice attenuation signals from interconnected detector subelements which cooperate to measure one complete slice in the region of interest constituted of one or more thin slices. Summing means, such as a summing amplifier, is coupled to the switching matrix for additively combining each output signals of the selectively interconnected detector subelements to produce a single slice-constituent signal which maps one slice in the region of interest. The one slice has a selectable thickness based upon the number of detector subelements interconnected in the switching matrix to contribute to the single slice-constituent signal. Image reconstruction means uses the single slice-constituent signal to produce an image, such as a CT image. The switching matrix can be adapted to produce additional sets of selectively interconnected signals in which case the one set of slice-constituent signals and such additional sets of slice-constituent signals each maps a different slice, in the region of interest, having a selectable thickness.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like numbers represent like parts throughout the drawings, and in which:

FIG. 1 is a perspective view of a CT system which employs the present invention;

DETAILED DESCRIPTION OF THE INVENTION

Figure 2B:
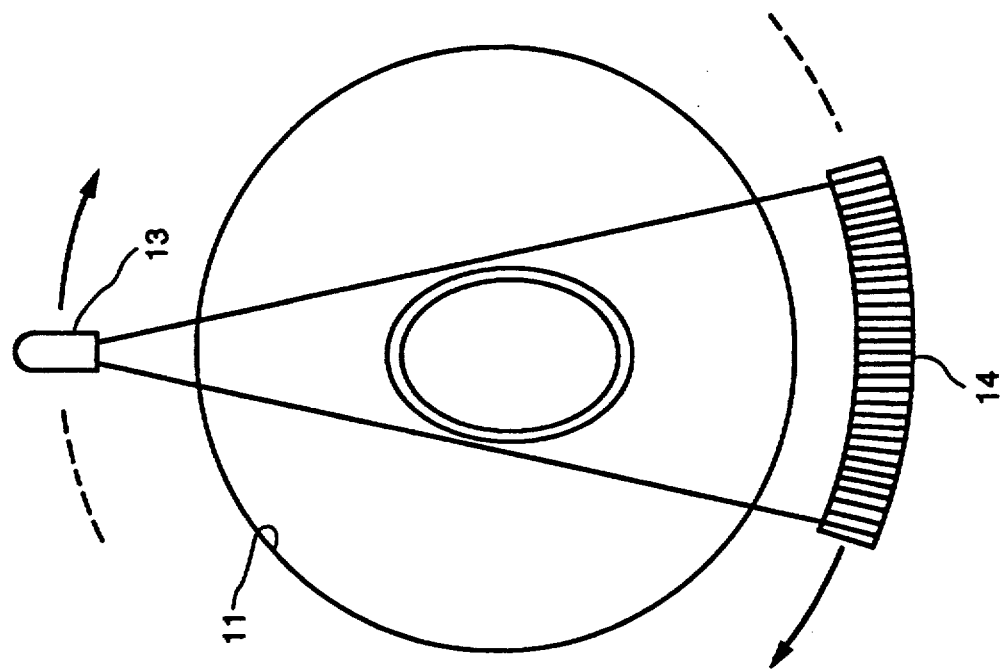
FIGS. 2a and 2b are schematic representations of two types of scanning techniques which may be employed in the CT system of FIG. 1.

As shown in FIG. 1, a CT system used to produce images of at least a region of interest of the human anatomy has a patient table 10 which can be positioned within the aperture 11 of a gantry 12. A source of imaging energy 13 which preferably produces highly collimated x-rays is mounted within the gantry 12 to one side of its aperture 11, and one or more detectors 14 are mounted to the other side of the aperture. As used herein, the expression "imaging energy" refers to various forms of radiant energy which can be used in imaging applications, x-ray energy being one example of a form of radiant energy. The x-ray source 13 and detectors 14 are revolved about the aperture 11 during a scan of the patient to obtain x-ray attenuation measurements from many different angles through a range of at least 180° of revolution.

Figure 2A:
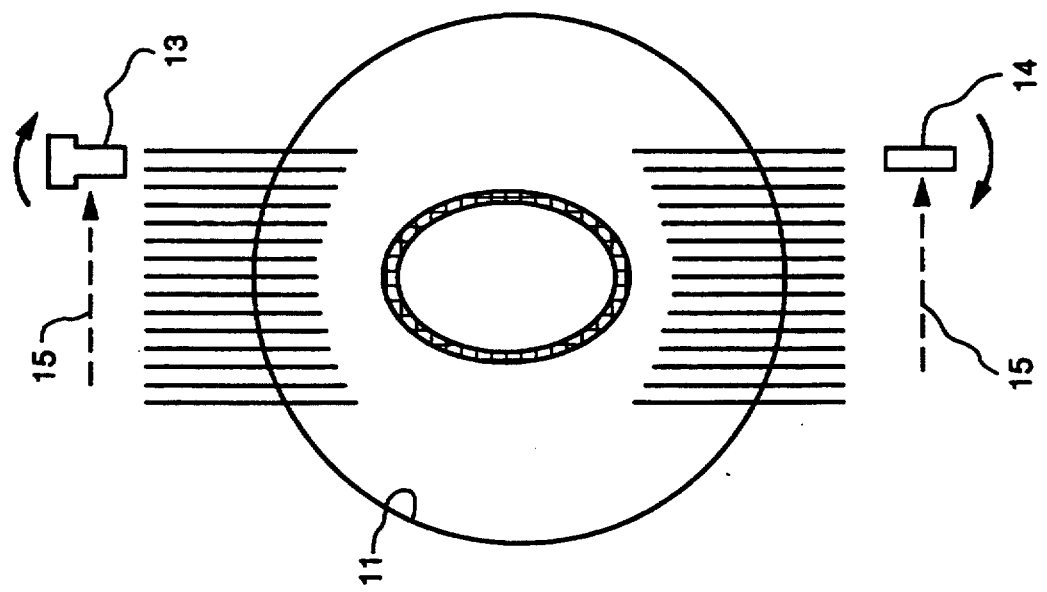

A complete scan of the patient is comprised of a set of x-ray attenuation measurements which are made at discrete angular orientations of the x-ray source 13 and detector 14. Each such set of measurements is referred to in the art as a "view" and the results of each such set of measurements is a transmission profile. As shown in FIG. 2A, the set of measurements in each view may be obtained by simultaneously translating the x-ray source 13 and detector 14 across the acquisition field of view, as indicated by arrows 15. As the devices 13 and 14 are translated, a series of x-ray attenuation measurements is made through the patient and the resulting set of data provides a transmission profile at one angular orientation. The angular orientation of the devices 13 and 14 is then changed (for example, incremented by 1°) and another view is acquired. An alternative structure for acquiring each transmission profile is shown in FIG. 2B. In this construction, the x-ray source 13 produces a fan-shaped beam which defines a plane that passes through the patient and impinges on a generally arcuate array of detectors 14 situated in the plane of the beam. In a conventional array detector, each detector in the array typically produces a separate attenuation signal and the signals from all the detectors are separately acquired to produce the transmission profile for the indicated angular orientation. As in the first structure, the x-ray source 13 and array detector 14 are then revolved to a different angular orientation and the next transmission profile is acquired.

Figure 3:
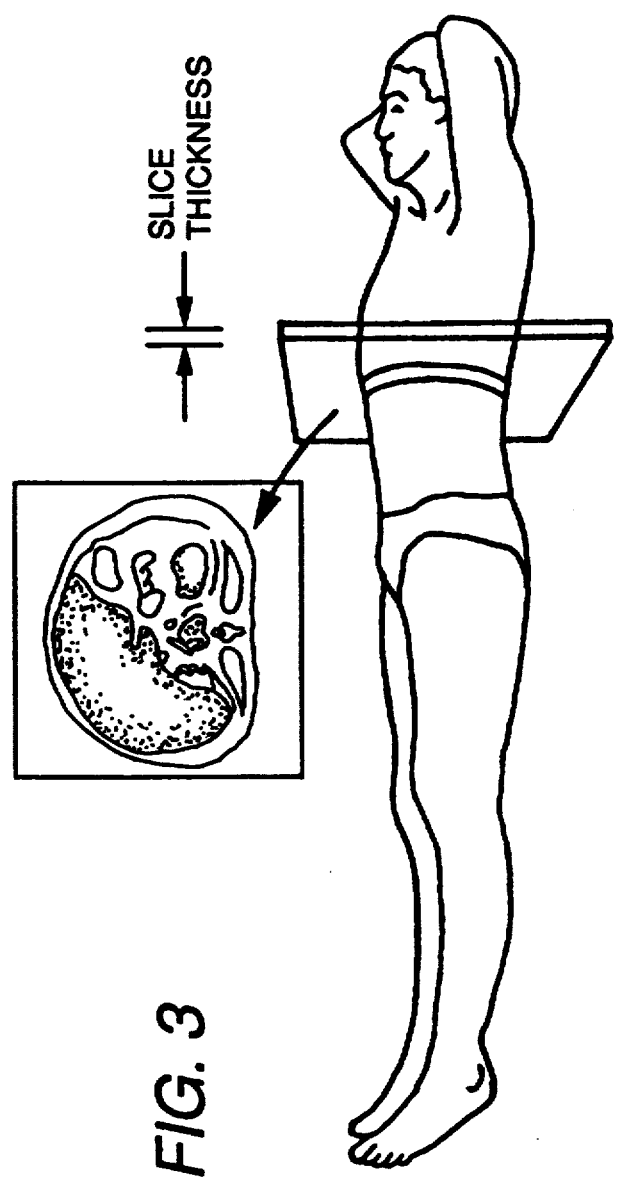
FIG. 3 is a pictorial view of a patient illustrating a typical image reconstructed from attenuation signals acquired with the system of FIG. 1.

The acquired transmission profiles are then used to reconstruct an image which indicates the x: ray attenuation coefficient of each voxel in the reconstruction field of view. These attenuation coefficients are converted to integers called "CT numbers," which are used to control the brightness of a corresponding pixel on a CRT display. As illustrated in FIG. 3, an image which reveals the anatomical structures in a slice taken through the patient and oriented normal to the axis of the gantry aperture is thus produced.

Figure 4:
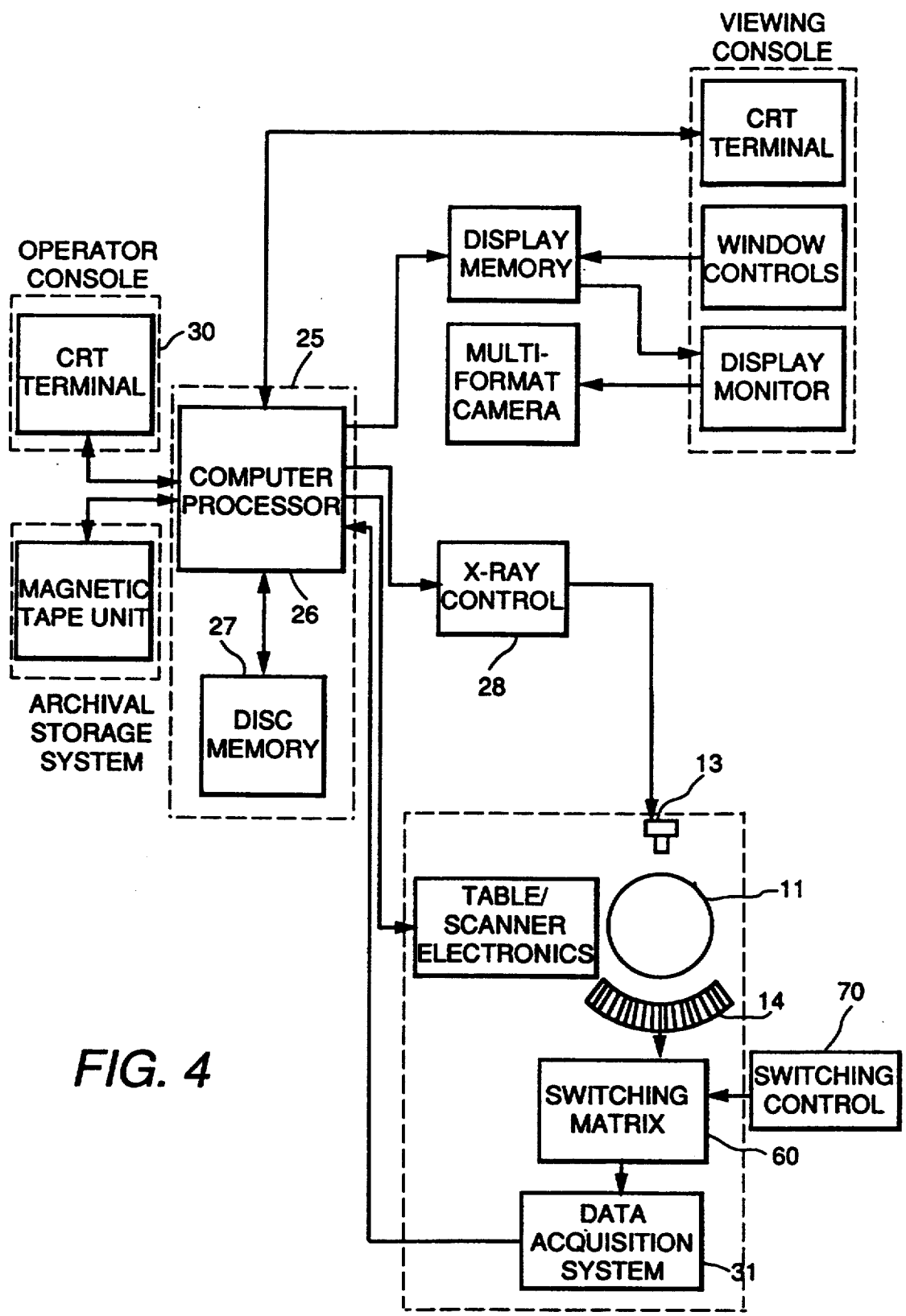
FIG. 4 is a block diagram of the CT system of FIG. 1.

Referring to FIG. 4, operation of the CT system is controlled by a programmed data processing system 25 which includes a computer processor 26 and a disc memory 27. Disc memory 27 stores the programs used by computer processor 26 in patient scanning and in image reconstruction and display. Memory 27 may also store on a short term basis the acquired data and the reconstructed image data. Computer processor 26 includes a general purpose computer with input and output ports suitable for connection to the other system elements, as shown and also includes an array processor such as that disclosed in U.S. Pat. No. 4,494,141.

An output port on computer processor 26 connects to an x-ray control circuit 28, which in turn controls both the high voltage and cathode current of x-ray source 13 to provide the correct dosage. The high voltage and cathode current are selected by an operator who enters the desired values together with the scan time and other scan parameters through an operator console 30. Computer processor 26 directs production of the x-rays in accordance with a scan program and the selected scan parameters.

The x-rays can be dispersed in a fan-shape, as previously described, and received by the array 14 of detectors positioned on the opposite side of gantry aperture 11. In the preferred embodiment there are about 800 detector elements, and each receives a single beam portion originating from x-ray source 13 and traversing a straight line path through at least a region of interest in a patient positioned in aperture 11. Array detector 14 can also include a group of reference cells at each of its ends that receive unattenuated x-rays from source 13. As will be described in more detail hereinafter, a controllable switching matrix 60 responsive to a suitable switching control device 70 receives each attenuation signal from array detector 14. Each electrical current formed in each detector element in cooperation with switching matrix 60 is collected as an analog electrical signal and converted into a digital number by a suitable A/D converter (not shown) in a data acquisition system 31. The digitized measurements from all the detectors which produce an attenuation signal make up a complete view. U.S. Pat. Nos. 4,112,303 and 4,115,695 disclose details of the gantry construction, and the data acquisition system is disclosed in U.S. Pat. No. 4,583,240. The digitized measurements from the data acquisition system 31 are processed in a well known manner to compensate for "dark currents", for uneven detector cell sensitivities and gains, and for variations in x-ray beam intensity throughout the scan. The digitized signals are in turn supplied to computer processor 26. It can be appreciated that a different number of detector cells can be employed to cover a smaller or larger field of view of the region of interest to be imaged.

Figures 5, 6:
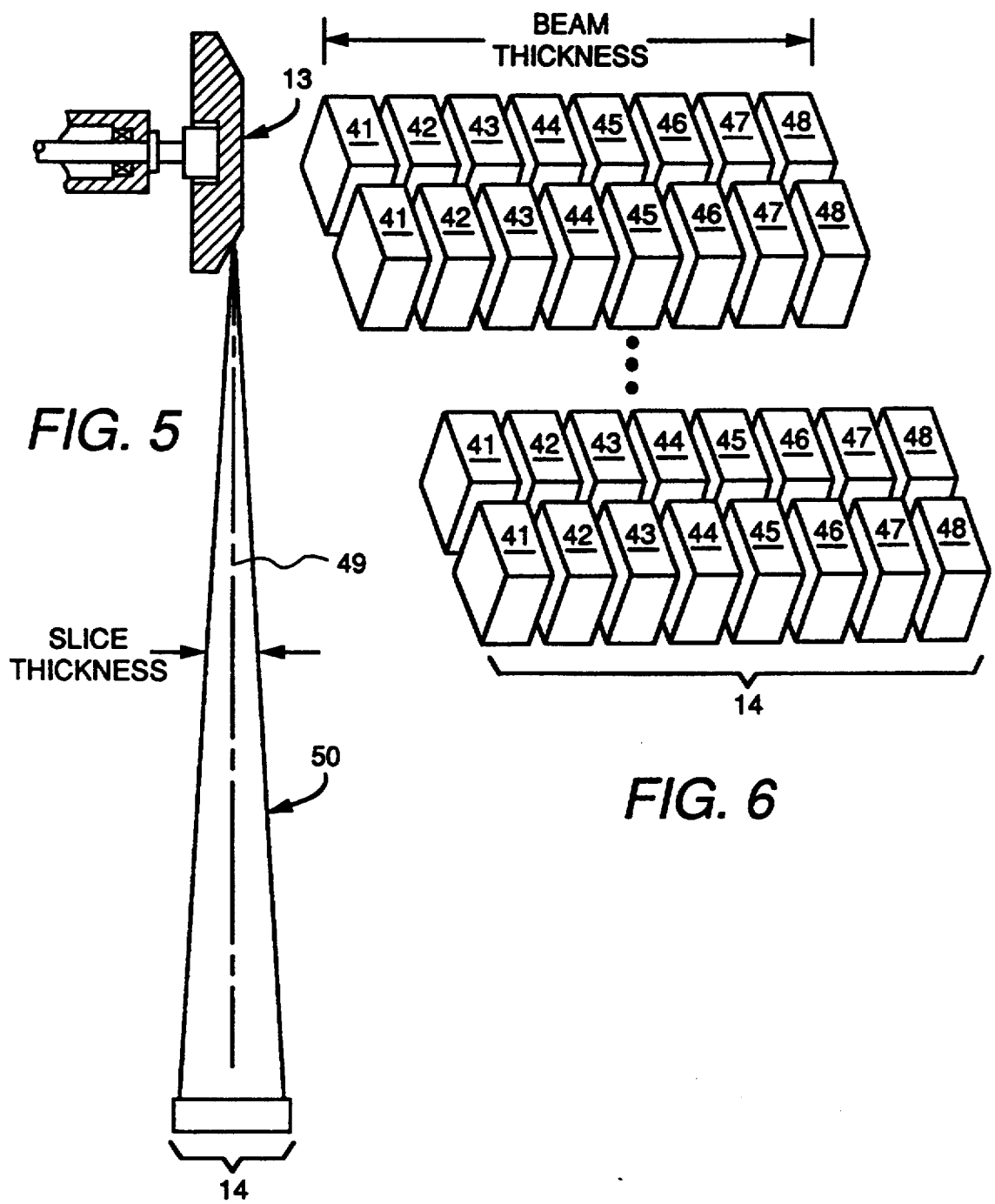
FIG. 5 is a schematic representation of the x-ray beam path, for the system of FIG. 1, showing its thickness.
FIG. 6 is a partial perspective view of a portion of the detectors used in the system of FIG. 1, showing the detector subelements disposed in the x-ray beam thickness direction.

As best seen in FIG. 5, the source of imaging energy 13 produces a beam of imaging energy 50, e.g., an x-ray beam of imaging energy, along a beam axis 49. The beam of imaging energy 50 has a predetermined thickness in a direction substantially orthogonal to beam axis 49. Thus it will be appreciated that in conventional scanners the beam thickness essentially determines the thickness of the patient slice which is to be imaged. As best seen in FIG. 6, each element of array detector 14 is composed of a set of separate detector subelements such as represented by the eight separate detector subelements 41-48. Subelements 41-48 are disposed along the beam thickness direction, and each receives a respective successive portion of x-ray beam 50 (FIG. 5) to produce a corresponding set of thin-slice attenuation signals, that is, each detector subelement produces an individual thin-slice attenuation signal which measures a thin slice (e.g., about 2 mm) in the region of interest to be imaged. Subelements 41-48 are disposed as close as possible to one another so that the thin slices which they measure are contiguous. In the preferred embodiment the number of detector subelements in each detector element is 16. Thus, in the preferred embodiment, array detector 14, by way of example and not of limitation, is a two-dimensional array detector comprising about 800×16 individual subdetector elements.

Those skilled in the art will appreciate that the x-ray beam is attenuated by an amount equal to the line integral of all the attenuations in its path through the region of interest to be imaged. If detector 14 is split into M subelements in the beam thickness direction, where the subelement size is small enough (e.g., about 2 mm along its thickness direction) so that there is no significant variation in attenuation within a voxel in the patient, then the thin-slice attenuation signal from each subelement represents a line integral which provides a substantially accurate measurement along a path between the x-ray source and the detector subelement and which can be reconstructed using processor 25 (FIG. 4) without degradation to image pixels. If the measured signal from successive detector subelements is additively combined, then the image reconstructed from the combined signal will map a slice in the region of interest having a selectable thickness based upon the number of successive detector subelements being additively combined.

Figure 7:
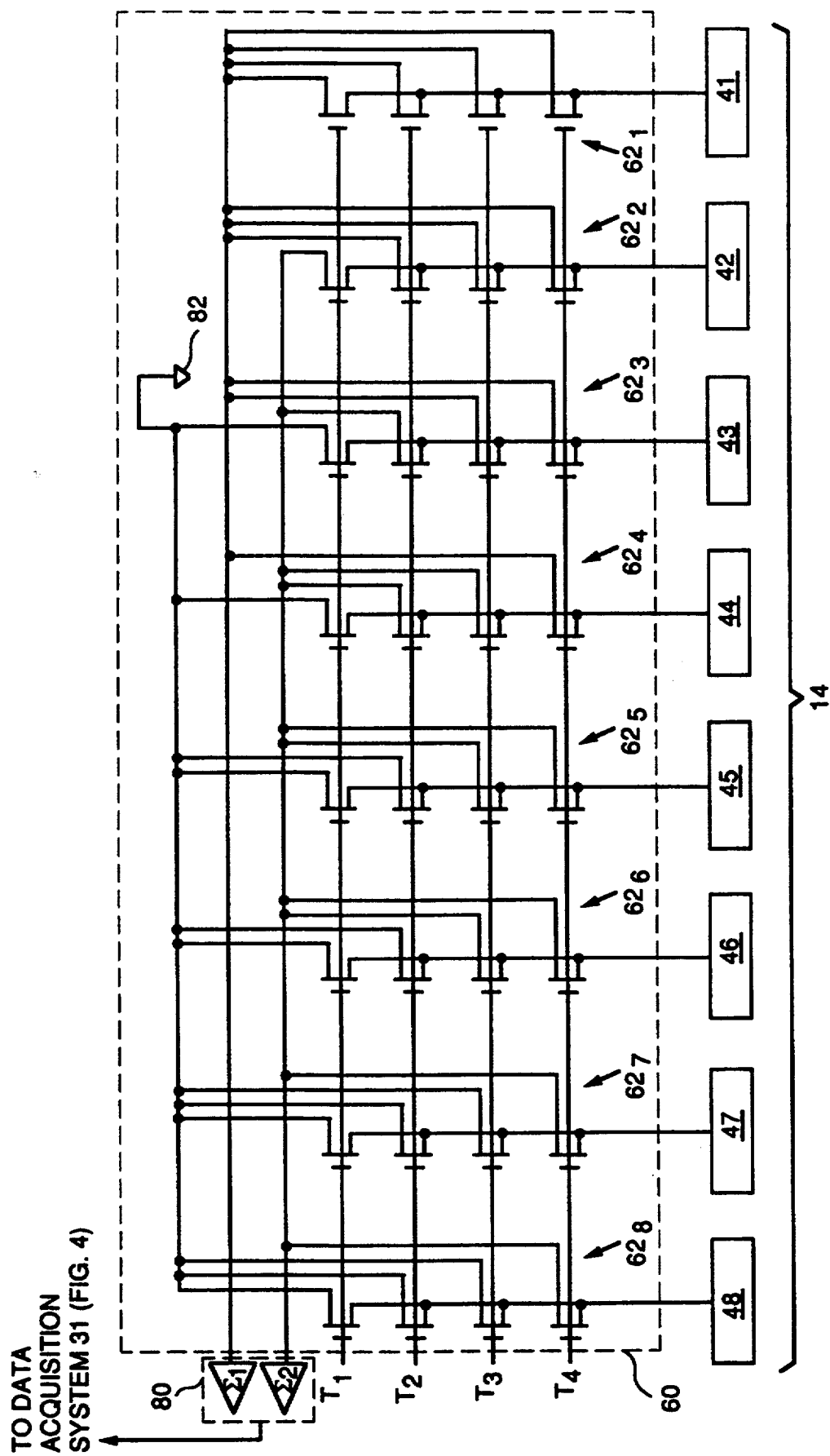
FIG. 7 is an electrical schematic diagram of an exemplary embodiment of a switching matrix in accordance with the present invention.
Figure 8B:
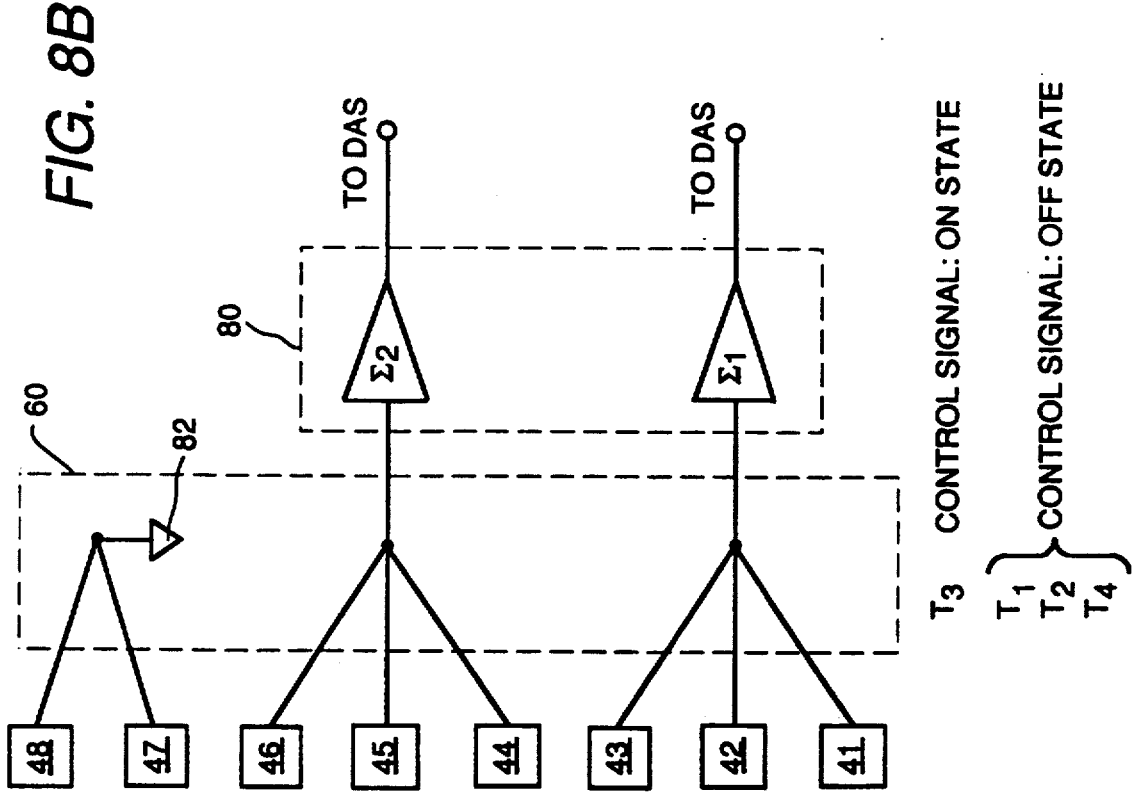
FIGS. 8a and 8b are block diagrams showing respective exemplary interconnections for the detector subelements using the switching matrix of FIG. 7.
Figure 8A:
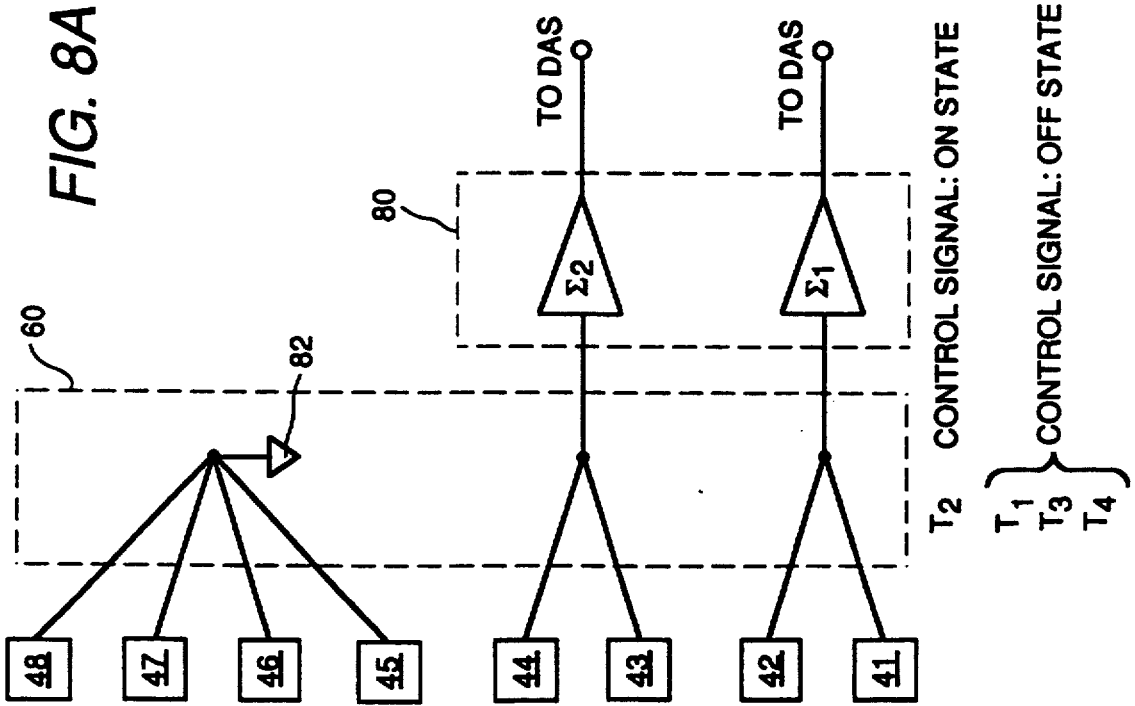

Referring to FIGS. 7, 8A and 8B, switching matrix 60 is coupled to the set of detector subelements 41-48 to receive each thin-slice attenuation signal produced therefrom. Switching matrix 60 is adapted to selectively interconnect a predetermined number of detector subelements to produce at least one set of interconnect thin-slice attenuation signals. Summing means 80 is coupled to switching matrix 60 for additively combining at least one set of interconnect thin-slice attenuation signals to produce a single slice-constituent attenuation signal measuring one slice in the region of interest. The summing means may comprise a single summing amplifier which supplies one single slice-constituent attenuation signal for such one slice in the region of interest. However, it will be appreciated that additional summing amplifiers can be used to map corresponding additional slices in the region of interest. For simplicity of explanation only two summing amplifiers $E_1$ and $E_2$ constitute the summing means illustrated in FIGS. 7, 8A and 8B and therefore the switching matrix and the two summing amplifiers can be operated to produce two separate slice-constituent signals each respectively mapping a different slice in the region of interest.

FIG. 7 illustrates an exemplary embodiment for switching matrix 60 which comprises a plurality of field effect transistors (FETs) or other suitable switching elements organized in respective sets $62_1$–$62_8$ each coupled to a respective detector subelement. Metal oxide semiconductor (MOS) transistors are preferred because of their substantially large impedance when in a non-conducting state. Each individual transistor in a given transistor set cooperates in response to a respective different control signal applied to its gate to pass the thin-slice attenuation signal from a given detector subelement either to the summing means 80 or to a reference voltage (e.g. ground 82). The applied control signal is part of a group of control signals $T_1$–$T_4$ which is received in parallel by each of the transistor sets. As shown in FIG. 7, each transistor in a respective one of the transistor sets has an input (e.g., a source terminal) coupled in common to one of the detector subelements to receive the thin-slice attenuation signal produced therewith. For example, each transistor in transistor set $62_8$ has its respective source terminal coupled in common to detector subelement 48 to receive the thin-slice attenuation signal produced by detector subelement 48. Further, at least one of the transistors in a respective transistor set has a respective output (e.g., a drain terminal) coupled to the summing means so that when such at least one transistor is actuated to a conducting state the received thin-slice attenuation signal is connected to the summing means. For example, in transistor set $62_8$, the transistor which receives the $T_4$ control signal has its drain terminal connected to the summing means so that when such transistor is actuated the thin-slice attenuation signal from detector subelement 48 is passed to the summing means and thereby detector subelement 48 contributes to the slice constituent signal supplied by summing amplifier $E_2$. Each remaining transistor in transistor set $62_8$, not connected to summing means 80, has its respective drain terminal connected to the reference voltage (e.g., ground 82) such that when a respective one of such remaining transistors in the transistor set is actuated, the attenuation signal from detector subelement 48 is disabled by the reference voltage 82, thereby preventing detector subelement 48 from contributing to any slice constituent signal produced by summing means 80. It will be appreciated that the function of the source and drain transistor terminals, as described above, was chosen by way of example and not of limitation being that such terminal functions can be easily reversed without affecting the operation of switching matrix 60.

In combination, the transistor sets cooperate in response to the control signals applied thereto so that each different slice in the region of interest measured with array detector 14 has a selectable thickness. The control signals are conveniently programmed such that whenever a given one of the control signals is provided in a selected state, (e.g., in an "on" state) that control signal uniquely causes a predetermined number of successive detector subelements to be interconnected to the summing means. In the exemplary embodiment of FIG. 7, four control signals $T_1$-$T_4$ are shown for simplicity of illustration, such that each slice in the region of interest measured by array detector 14 can have four different thicknesses depending on which control signal is energized. Thus, in operation, transistor sets $62_1$-$62_8$ advantageously cooperate in response to the control signals to interconnect a predetermined number of the detector subelements to summing means 80 or to reference voltage 82.

FIGS. 8A and 8B illustrate respective exemplary modes of operation for the embodiment of the switching matrix shown in FIG. 7. In particular, FIG. 8A illustrates the mode of operation of switching matrix 60 when the $T_2$ control signal is present or "on" while signals $T_1$, $T_3$ and $T_4$ are absent or "off", that is, each transistor receiving the $T_2$ control signal is in a respective conducting state to produce any received thin-slice attenuation signal while each transistor respectively receiving any of control signals $T_1$, $T_3$ and $T_4$ is in a respective nonconducting state. As shown in FIG. 8A, switching matrix 60 produces two different sets of interconnect thin-slice attenuation signals. The one set of interconnect thin-slice attenuation signals from detector subelements 41 and 42 contributes to the respective single slice constituent attenuation signal supplied by summing amplifier $E_1$ to data acquisition system 31. The additional set of interconnect thin-slice attenuation signals from detector subelements 43 and 44 contributes to the respective single slice constituent attenuation signal supplied by summing amplifier $E_2$ to data acquisition system 31. Conversely, detector subelements 45-48 are interconnected to the reference voltage and hence they do not contribute to any single slice constituent attenuation signal.

FIG. 8B illustrates the mode of operation of switching matrix 60 in response to the $T_3$ control signal being present (e.g., "on") while the $T_1$, $T_2$ and $T_4$ control signals are absent (e.g., "off"). Similar to the example described in the context of FIG. 8A, again each of the two sets of interconnect thin-slice attenuation signals is supplied to a respective one of the summing amplifiers, however, it will be appreciated that in this example each set of interconnect thin-slice attenuation signals is constituted of thin-slice attenuation signals from three successive detector subelements and therefore the thickness of each of the two slices measured by each respective single attenuation signal is one half thicker than for each of the respective slices obtained in the example illustrated in FIG. 8A. To insure that the signal output level from a given summing amplifier remains substantially uniform regardless of the number of detector subelements interconnected thereto, each summing amplifier is preferably designed to have a selectable gain so as to provide a suitable attenuation factor, in accordance with the number of detector subelements interconnected thereto. For example, if n (n being a positive integer) detector subelements are interconnected to a given summing amplifier, the amplifier-gain ($\gamma$) can be selected to be $\gamma = 1/n$ and this manner each respective slice-constituent signal produced by a respective summing amplifier is suitable attenuated to have a substantially uniform level. Thus, in the mode of operation illustrated in FIG. 8A, the individual gain of amplifiers $E_1$ and $E_2$ would be one half whereas in the mode of operation illustrated in FIG. 8b, the individual gain of amplifiers $E_1$ and $E_2$ would be one third.

In each of the above-described modes of operation, each respective slice-constituent attenuation signal is supplied to data acquisition system 31 where it is converted to digital form, and then to data processing system 25 where it is processed to provide an image data so as to enable reconstruction of a respective CT image. Data processing system 25 is coupled to a suitable display device, such as a CRT terminal and the like, which can be part of operator console 30 (FIG. 4) to display the CT image. Briefly, before reconstructing the image from the attenuation values, respective filtering and Fourier transformation steps are performed before performing a conventional back projection which allows control of the pixel brightness in the reconstructed image as described in U.S. Pat. No. 5,241,576.

It will be appreciated that switching matrix 60, as illustrated in FIG. 7, can be readily expanded to handle a larger number of detector subelements, such as sixteen, for example. It will be further appreciated that the switching matrix can be constructed integral to array detector 14 in order to reduce cabling requirements. Other constructions for switching matrix 60 can provide equally advantageous operation. For example, the switching matrix can be constructed on a separate integrated circuit module or can be constructed as part of data acquisition system 31 (FIG. 4). Preferably, each detector subelement comprises a photodiode which includes suitable means for receiving a fixed bias voltage so as to provide good linearity characteristics for each of the detector subelements.

Although various specific constructions have been given for the present invention, it is to be understood that these are for illustrative purposes only. Various modifications and adaptations will be readily apparent to those skilled in the art without departing from the substance or scope of the invention. Accordingly, it is intended that the invention be limited only by the spirit and scope of the claims appended hereto.

What is claimed is:

1. A computerized tomography system for imaging at least a region of interest in a body, said system comprising:

a source of imaging energy for producing a beam of imaging energy substantially along a beam axis, said beam of imaging energy having a predetermined thickness in a direction orthogonal to said beam axis;

an array detector positioned to receive said beam of imaging energy, said array detector including a set of detector subelements aligned with each other along said beam thickness direction to receive successive portions of said beam of energy along its thickness direction to produce a corresponding set of thin-slice attenuation signals;

a switching matrix coupled to said set of detector subelements to receive each thin-slice attenuation signal and to selectively interconnect a predetermined number of respective ones of said detector subelements to supply at least one set of interconnect thin-slice attenuation signals corresponding to one slice of said region of interest;

summing means coupled to said matrix for additively combining output signals of the selectively interconnected detector subelements to produce a single slice-constituent attenuation signal having a selectable thickness determined by said predetermined number of detector subelements interconnected with said switching matrix; and image reconstruction means for receiving said single slice-constituent signal and producing an image in response thereto.

2. The computerized tomography system of claim 1 wherein said switching matrix comprises a plurality of field effect transistor sets, each transistor in said respective one of said transistor sets having an input coupled in common to one of said detector subelements, at least one of said transistors in said respective one of said transistor sets having a respective output coupled to said summing means such that when said at least one transistor is actuated the attenuation signal from said one detector subelement is passed to said summing means so as to contribute to said single slice-constituent signal, each remaining transistor in said respective one of said transistor sets having a respective output coupled to a reference voltage such that when any one of the remaining transistors in said respective one of said transistor sets is actuated, the attenuation signal from said one detector subelement is terminated so as to prevent said one detector subelement from contributing to said single slice-constituent signal.

3. The computerized tomography system of claim 2 wherein each transistor in a respective one of said transistor sets is a metal oxide semiconductor field effect transistor.

4. The computerized tomography system of claim 1 further comprising a display coupled to said image reconstruction means for displaying said image.

5. The computerized tomography system of claim 1 wherein said source of imaging energy comprises an x-ray source.

6. The computerized tomography system of claim 1 wherein said beam of imaging energy comprises a fan beam of x-rays, said fan beam defining a plane that passes through said body.

7. The computerized tomography system of claim 6 wherein said array detector comprises a two-dimensional array of detector elements situated in the plane defined by said fan beam, and each one of said detector elements comprises a set of detector subelements.

8. The computerized tomography system of claim 2 wherein said switching matrix is adapted to supply additional sets of interconnect thin-slice signals, said at least one set and said additional sets of interconnect thin-slice signals each mapping a different slice of said region of interest, respectively.

9. The computerized tomography system of claim 8 wherein said plurality of transistor sets cooperates in response to predetermined control signals applied thereto to selectively interconnect successive ones of said detector subelements so that each different slice of said region of interest has a selectable thickness.

10. The computerized tomography system of claim 8 wherein said summing means comprises a plurality of summing amplifiers, each one of said summing amplifiers being coupled to receive a corresponding one of said at least one set and said additional sets of interconnect thin-slice signals for producing a corresponding plurality of single slice-constituent signals, and wherein said image reconstruction means comprises means for producing a corresponding plurality of images.

11. The computerized tomography system of claim 10 wherein each respective one of said summing amplifiers includes means for selectively attenuating each respective one of said single slice-constituent signals.

12. The computerized tomography system of claim 1 wherein said array detector and said switching matrix are integral to one another.

13. The computerized tomography system of claim 1 wherein each one of said detector subelements includes means for receiving a predetermined bias voltage.

14. An imaging system for imaging at least a region of interest in a body, said system comprising:
a source of imaging energy for producing a beam of imaging energy substantially along a beam axis, said beam of imaging energy having a predetermined thickness in a direction orthogonal to said beam axis;
an array detector positioned to receive said beam of imaging energy, said array detector including a set of detector subelements aligned with each other along said beam thickness direction to receive successive portions of said beam of energy along its thickness direction to produce a corresponding set of thin-slice attenuation signals;
a switching matrix coupled to said set of detector subelements to receive each thin-slice attenuation signal and to selectively interconnect a predetermined number of respective ones of said detector subelements to supply at least one set of interconnect thin-slice attenuation signals corresponding to one slice of said region of interest;
summing means coupled to said matrix for additively combining output signals of the selectively interconnected detector subelements to produce a single slice-constituent attenuation signal having a selectable thickness determined by said predetermined number of detector subelements interconnected with said switching matrix;
image reconstruction means for receiving said single slice-constituent signal and producing an image in response thereto; and
a display coupled to said image reconstruction means for displaying said image.

15. The imaging system of claim 14 wherein said source of imaging energy comprises an x-ray source and said imaging system is a computerized tomography system.

16. The imaging system of claim 15 wherein said beam of imaging energy comprises a fan beam of x-rays, said fan beam defining a plane that passes through said body.

17. The imaging system of claim 16 wherein said array detector comprises a two-dimensional array of detector elements situated in the plane defined by said fan beam, and each one of said detector elements comprises a set of detector subelements.

18. The imaging system of claim 15 wherein each one of said detector subelements includes means for receiving a predetermined bias voltage.

19. The imaging system of claim 14 wherein said array detector and said switching matrix are integral to one another.

20. The imaging system of claim 14 wherein said switching matrix comprises a plurality of field effect transistor sets, each transistor in said respective one of said transistor sets having an input coupled in common to one of said detector subelements, at least one of said transistors in said respective one of said transistor sets having a respective output coupled to said summing means such that when said at least one transistor is actuated the attenuation signal from said one detector subelement is passed to said summing means so as to contribute to said single slice-constituent signal, each remaining transistor in said respective one of said transistor sets having a respective output coupled to a reference voltage such that when any one of the remaining transistors in said respective one of said transistor sets is actuated, the attenuation signal from said one detector subelement is terminated so as to prevent said one detector subelement from contributing to said single slice-constituent signal.

21. The imaging system of claim 20 wherein each transistor in a respective one of said transistor sets is a metal oxide semiconductor field effect transistor.

22. The imaging system of claim 20 wherein said switching matrix is adapted to supply additional sets of interconnect thin-slice signals, said at least one set and said additional sets of interconnect thin-slice signals each mapping a different slice of said region of interest, respectively.

23. The imaging system of claim 22 wherein said plurality of transistor sets cooperates in response to predetermined control signals applied thereto to selectively interconnect successive ones of said detector subelements so that each different slice of said region of interest has a selectable thickness.

24. The imaging system of claim 22 wherein said summing means comprises a plurality of summing amplifiers, each one of said summing amplifiers being coupled to receive a corresponding one of said at least one set and said additional sets of interconnect thin-slice signals for producing a corresponding plurality of single slice-constituent signals, and wherein said image reconstruction means comprises means for producing a corresponding plurality of images.

25. The imaging system of claim 24 wherein each respective one of said summing amplifiers includes means for selectively attenuating each respective one Of said single slice-constituent signals.

* * * * *